United States Patent [19]
Hattori et al.

[11] Patent Number: 5,895,751
[45] Date of Patent: Apr. 20, 1999

[54] METHOD AND KIT FOR TESTING MICROBIAL DRUG SENSITIVITY, AND METHOD AND KIT FOR MEASURING MINIMUM INHIBITING CONCENTRATION FOR MICROORGANISMS

[75] Inventors: Noriaki Hattori; Moto-o Nakajima; Keiko Yajitate, all of Chiba-ken, Japan

[73] Assignee: Kikkoman Corporation, Chiba-Ken, Japan

[21] Appl. No.: 08/968,548

[22] Filed: Nov. 12, 1997

[30] Foreign Application Priority Data

Nov. 14, 1996 [JP] Japan ................... 8-316937

[51] Int. Cl.$^6$ ............... C12Q 1/02; C12Q 1/04; C12Q 1/18; C12Q 1/66
[52] U.S. Cl. ................ 435/8; 435/4; 435/21; 435/29; 435/32; 435/34; 435/975
[58] Field of Search ................ 435/4, 34, 975, 435/32, 8, 21, 29

[56] References Cited

FOREIGN PATENT DOCUMENTS

| 0781 851 | 7/1997 | European Pat. Off. . |
|---|---|---|
| 2 059 990 | 7/1984 | United Kingdom . |
| WO 94 28169 | 12/1994 | WIPO . |

OTHER PUBLICATIONS

"Chemical Sensitive Test Microbe Antibiotic Culture Medium Contain Chemical Determine Amount ATP Prefer Luciferin Luciferase Compare Control Amount", Derwent Publications, Ltd., London, GB, Dec. 22, 1992 (Abstract).

Saunders et al., "Metabolism and action of neplanocin A in Chinese hamster ovary cells", *Biochem. Pharmacol.* (1985), 34 (15), 2749–54.

*Primary Examiner*—Johnny F. Railey, II
*Attorney, Agent, or Firm*—Fish & Richardson P.C.

[57] ABSTRACT

There are provided a method and a kit for testing microbial drug resistance and a method and a kit for measuring minimum inhibitory concentration for a microorganism, in which highly reliable evaluation results are obtained by preventing false evaluation based on false-resistance of microorganisms to a drug. The method of testing microbial drug sensitivity comprises inoculating and culturing a microorganism in a drug-containing medium to obtain a medium containing the microorganism morphologically transformed by the influence of the drug, adding an ATP elution agent and an ATP deletion agent to the culture to delete the eluted ATP and other ATP in the medium, and comparing the amount of ATP in the microorganism remaining in the culture with the amount of ATP in the microorganism separately cultured in a medium not containing said drug and treated in the same manner as above. The method of measuring minimum inhibitory concentration for a microorganism is carried out in the same manner as above.

13 Claims, 1 Drawing Sheet

METHOD AND KIT FOR TESTING MICROBIAL DRUG SENSITIVITY, AND METHOD AND KIT FOR MEASURING MINIMUM INHIBITING CONCENTRATION FOR MICROORGANISMS

FIELD OF THE INVENTION

The present invention relates to an improvement of a method of testing microbial drug sensitivity using a conventional ATP method and in particular to a method and a kit for testing microbial drug sensitivity and a method and a kit for measuring minimum inhibitory concentration for microorganisms, in which highly reliable evaluation results are obtained by preventing false evaluation based on false-resistance of microorganisms to drugs. The method of testing microbial drug sensitivity is also as antimicrobial susceptibility test of a drug.

BACKGROUND OF THE INVENTION

The ultimate object of a drug resistance test in chemotherapy is to evaluate the effectiveness of drugs against causative microorganisms (also referred to hereinafter as pathogen) causing of infections for achieving appropriate drug administration.

On the other hand, there are cases where the pathogen has been rendered drug-resistant because of use of a large amount of anti-infection agents for a long period of time.

In this case, for the success of treatment of infections it is very important to ascertain the properties of the pathogen of interest, particularly with respect to drug sensitivity or drug resistance.

However, conventional drug sensitivity tests such as the disk methods micro-liquid dilution method (liquid medium dilution method) and agar plate dilution method (which are collectively referred to hereinafter as the conventional method) are disadvantaged in that because at least 16- to 20-hour incubation is required, evaluation of the results is obtained at the earliest the day after the examination is initiated, although highly reliable evaluation results can be obtained.

Under these circumstances, there is a demand for the advent of a method of testing microbial drug resistance that can be evaluated more rapidly.

Conventionally, a method of evaluating drug resistance by culturing a microorganism in a drug-containing medium for 3 to 5 hours and comparing the amount of ATP in the microorganism and the amount of ATP in the microorganism separately cultured in a medium not containing the drug is known as a method of testing microbial drug resistance that can be evaluated more rapidly (referred to hereinafter as the method of testing microbial drug sensitivity using the conventional ATP method) (Japanese Patent Appln. LOP Publication No. 370100/92).

This prior art method uses a luciferin-luciferase system luminescent reagent for the measurement of ATP levels. The following advantages are realized for this method: the detection limit of microorganisms is as high as $10^3$ CFU/ml which is very sensitive; the proliferation and deproliferation of microorganisms can be observed just after inoculation in the case of a drug sensitivity test where the amount of microorganisms inoculated into the medium is $10^5$ CFU/ml; and the culture time can be drastically reduced as compared with the conventional method (H. Hojer, L. Nilsson, S. Aosehn and A. Thore, Scand. J. Infect. Dis., Suppl., 9, 58–61, 1976 and A. Thore, L. Nilsson, E Hojer, S. Ansehn and L. Brote, Acta Path. Microbiol. Scand. Sect. B, 85, 161–166, 1977).

However, the results in this method of testing microbial drug sensitivity using the conventional ATP method often give contrary results i.e. false-resistant results when Gram-negative bacilli such as *Pseudomonas aeruginosa* etc. are examined for their resistance to β-lactam antibiotics (Vellend, H., S. A. Tuttle, M. Barza, L. Weinstein, G. L. Picciolo and E. W. Chappelle, NASA Technical Notes 1974).

That is, the method of testing drug sensitivity using the conventional ATP method has a major drawback of giving false evaluation based on false-resistance of microorganisms to drugs, thus undermining the reliability of evaluation results.

As described in more detail below, it has been believed that the false-resistance give by the method of testing drug sensitivity using the conventional ATP method is caused by the fact that the microorganisms of interest, even while undergoing morphological transformation into, for example, spheroplast and filament forms by the influence of the drug, remain alive.

That is, this false-resistance is observed particularly frequently with β-lactam antibiotics which inhibit the synthesis of cell walls in a microorganism, and if the microorganism is cultured in the presence of these antibiotics, the microorganism will survive initially while undergoing morphological transformation into spheroplast or filament forms, for example, but if culturing is further continued, the microorganism will finally lyse and perish owing to the difference in osmotic pressure in the surroundings. Accordingly, the microorganism while undergoing morphological transformation, is alive for 3 to 5 hours, which is a period of time required by the method to test for microbial drug resistance using the conventional ATP method, so in this case the result will be "resistant", whereas the microorganism perishes after 16 to 20 hours, which is a period of time required by the conventional method, so in this case the result will be "sensitive". Hence, false-resistance will be given by the method of testing microbial drug resistance using the conventional ATP method.

As countermeasures against this false-resistance evaluation by the method of testing microbial drug sensitivity using the conventional ATP method, there are known methods in which microorganisms morphologically transformed into forms of filament, spheroplast etc., by the influence of a drug are selectively lysed by diluting a medium or by using a medium of low osmotic pressure (P. F. Wheat, J. G. M. Hastings and R. C. Spencer, J. Med. Microbiol., 25, 95–99, 1988 and E. G. Hornsten, L. E. Nilsson, H. Elwing, and L. Lundstrom, Diagn. Microbiol. Infect. Dis., 12, 171–175, 1989).

However, these attempts are effective where the target is a specific microorganism, but these are not suitable for achieving the present object of the drug sensitivity test directed to a wide spectrum of microorganisms.

A method of measuring minimum inhibitory concentration using the conventional ATP method also has a major drawback of giving false evaluation based similarly on the result of false-resistance, thus undermining the reliability of evaluation results.

In addition, similar disadvantages exist in a method of measuring minimum bactericidal concentration (MBC), that is, the minimum amount of a drug at which the growth inhibitory effect of the drug on a microorganism acts in a bactericidal manners as well as in a method of measuring post antibiotic effect (PAE), that is, the effect of a drug which after exposure of a microorganism to the drug for a few hours, that lasts even in the absence of the drug.

Measurement of MBC is carried out by culturing a microorganism overnight in a drug-containing medium and then culturing it again in a drug-free medium to determine the minimum concentration of the drug at which the re-growth of the microorganism does not occur.

Measurement of PAE is carried out by culturing a microorganism for a few hours (about 2 hours) in a drug-containing medium, then diluting the culture 1000 times with a drug-free medium, and culturing the microorganism again, and determining the time at which the re-growth of the microorganism occurs.

SUMMARY OF THE INVENTION

The object of the present invention is to provide a method of testing microbial drug resistance and a method of measuring minimum inhibitory concentration for a microorganism by the ATP method that is applicable to a wide spectrum of microbial species, is free of false evaluation based on false-resistance of microorganisms, and gives highly reliable evaluation results.

As a result of their earnest effort to solve the above problems, the present inventors found that EDTA (chelating agent), Triton X-100, Tween 20, Tween 40, ANHITOL (surface active agent), 2-amino-2-methyl-1,3-propanediol, 2-amino-2-methyl-1-propanol, ethylamine and ethanolamine (amines) can selectively lyse a microorganism morphologically transformed into spheroplast and filament forms by the influence of a drug, thus eluting ATP from it.

The eluted ATP and other background ATP derived from non-microbial materials are deleted, and then the amount of ATP in the microorganism remaining in the medium is compared with the amount of ATP in the microorganism separately cultured in a drug-free medium, so that false evaluation based on false-resistance of microorganisms to a drug is prevented and reliable evaluation results are obtained. On the basis of these findings, the present inventors completed the present invention.

That is, the present invention is a method of testing microbial drug sensitivity, comprising the following steps:

(1) inoculating and culturing a microorganism in a drug-containing medium;

(2) adding a first ATP elution agent and an ATP deletion agent to the resulting culture;

(3) adding a second ATP elution agent to the culture obtained in step (2) above and determining the eluted ATP;

(4) inoculating and culturing a microorganism in a control medium not containing said drug, and carrying out steps (2) and (3) above to determine the ATP in the microorganism; and (5) comparing the amounts of ATP obtained in steps (3) and (4) above.

In additions the present invention relates to a kit for testing microbial drug sensitivity, comprising at least (A) a first ATP elution agent and (B) an ATP deletion agent. Further, the present invention relates to a kit for testing microbial drug sensitivity, comprising (A) a first ATP elution agent, (B) an ATP deletion agent, (C) a second ATP elution agent, and (D) a luciferin-luciferase system luminescent reagent.

Furthermore, the present invention relates to a method of measuring minimum inhibitory concentration for a microorganism, comprising the following steps:

(1) inoculating and culturing a microorganism in a drug-containing medium;

(2) adding a first ATP elution agent and an ATP deletion agent to the resulting culture;

(3) adding a second ATP elution agent to the culture obtained in step (2) above and determining the eluted ATP;

(4) inoculating and culturing a microorganism in a control medium not containing said drug, and carrying out steps (2) and (3) above to determine the ATP in the microorganism; and (5) comparing the amounts of ATP obtained in steps (3) and (4) above.

In addition, the present invention relates to a kit for measuring minimum inhibitory concentration for a microorganism, comprising at least (A) a first ATP elution agent and (B) an ATP deletion agent.

Further, the present invention relates to a kit for measuring minimum inhibitory concentration for a microorganism, comprising (A) a first ATP elution agent, (B) an ATP deletion agent, (C) a second ATP elution agents and (D) a luciferin-luciferase system luminescent reagent.

DETAILED DESCRIPTION OF THE INVENTION

Figure 1:
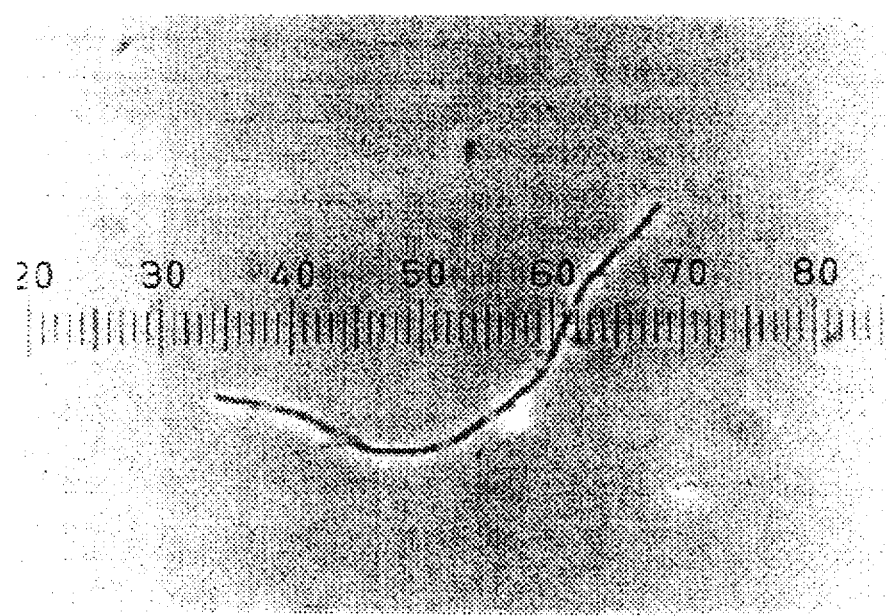
FIG. 1 is an optical micrograph (magnification: 100X) showing the form of a microorganism cultured for 3 hours in a medium containing antibiotic PIPC. Cells rendered thin and long (filament form) by the influence of the antibiotic are observed in the central vicinity.

In the first step of the present inventions a microorganism examined is inoculated into a drug-containing medium and cultured.

The drugs used herein may be any arbitrary drug directed to a microbial drug sensitivity test for usual microorganisms, and examples are antibiotics, antibacterial agents, antifungus agents etc.

Depending on combinations of these microorganisms with drugs, there are cases where while the results in the conventional method are drug-sensitive, the results in the method of testing microbial drug sensitivity using the conventional ATP method give opposite results (false-resistant), so the evaluation results may differ therebetween.

The method of testing microbial drug sensitivity according to the present invention contributes greatly to such cases where the evaluation results differ between the conventional method and the method of testing microbial drug sensitivity using the conventional ATP method.

The effect of the present invention is particularly outstanding when β-lactam antibiotics are used, so the β-lactam antibiotics are particularly preferable for the present invention.

The medium includes solid, liquid or semi-liquid (paste) nutrient media suitable for growth and multiplication of the microorganism examined.

The medium may be any natural, synthetic or semi-synthetic medium.

Microorganism is cultured at a temperature, time and pH suitable for growth of the microorganism examined, preferably 15 to 50° C., 30 minutes to 30 days and pH 4 to 10.

The microorganisms examined to which the present invention is applied include arbitrary microorganisms such as bacteria, yeast, fungi, basidiomycetes and tubercle bacillus etc.

The method of testing microbial drug sensitivity for tubercle bacillus used to require 2 to 3 months, but according to the present invention, the testing can be done in 30 days, approximately.

The effect of the present invention is particularly outstanding where the microorganisms examined are those (e.g. Gram-negative bacilli such as *Pseudomonas aeruginosa* etc.) judged to be sensitive by the conventional method while often judged to be resistant (false-resistant) by the method of testing drug resistance using the conventional ATP method, therefore, *Pseudomonas aeruginosa* is particularly preferable.

*Pseudomonas aeruginosa* is known to be a causative microorganism causing septicemia, meningitis, bronchitis, pneumonia, traumatic infections (traumatic infections caused by various degrees of burns, bedsores etc.), and it is very important to grasp the drug sensitivity or resistance of this microorganism at an early stage in order to treat such infections.

When the microorganisms examined are inoculated into a drug-containing medium and cultured, some microorganisms undergo morphological transformation into, for examples filament and spheroplast forms.

That is, the microorganisms are present as a mixture of transformed forms and normal forms in the medium.

Then, the microorganisms of transformed forms caused by the influence of the drug are selectively lysed, and the first ATP elution agent for elution of ATP and the ATP deletion agent are added to the medium, so that the eluted ATP and other background ATP derived from non-microbial materials are deleted.

The first ATP elution agent in the present invention is an elution agent causing elution of ATP from microorganisms whose forms have been transformed, but not causing elution of ATP from microorganisms whose forms are not transformed, and examples are at least one of a chelating agent, surface active agent and amine.

Among these, the chelating agent is at least one of ethylenediaminetetraacetic acid, nitrilotriacetic acid, bis-(O-aminophenoxy)-ethane-N,N,N',N'-tetraacetic acid, ethyleneglycol-bis-(β-aminoethylether)N,N,N',N'-tetraacetic acid, trans-1,2-diaminocyclohexanetetraacetic acid, diethylenetriaminepentaacetic acid, citric acid, arginine, hypoxanthine, 4,5-dihydroxybenzene-1,3-disulphonic acid, sodium phosphate glass, and crown-ether-type compounds, as well as derivatives and precursors thereof.

These are used preferably in the range of 0.5 to 50 mM.

Further, the surface active agent is at least one of non-ionic surface active agents such as Triton X-100, Tween 20, Tween 40 etc., anionic surface active agents and cationic surface active agents and zwitterionic surface active agents such as ANHITOL etc.

These are used preferably in the following concentration ranges:

Triton X-100 (non-ionic surface active agent): 0.0005 to 0.05%;

Tween 20 (non-ionic): 0.01 to 0.5%;

Tween 40 (non-ionic). 0.01 to 0.5%; and

ANHITOL (zwitterionic surface active agent): 0.002 to 0.2%.

The amine is at least one of 2-amino-2-methyl-1,3-propanediol, 2-amino-2-methyl-1-propanol, ethylamine, ethanolamine, and analogues and derivatives thereof.

Among these, 2-amino-2-methyl-1,3-propanediol and 2-amino-2-methyl-1-propanol are preferable.

These are used preferably in the range of 0.01 to 5%.

By using a suitable drug concentration determined by the type of medium microorganism and drugs used, the first ATP elution agent can selectively lyse the morphologically transformed microorganism to elute ATP from the microorganism.

Then, the ATP deletion agent is added to this medium so that the ATP eluted from the microorganism and other background ATP derived from non-microbial materials are deleted.

The ATP deletion agent includes arbitrary enzymes that decompose ATP, such as adenosine nucleotide deaminase, ATPase, adenosine phosphate deaminase, apyrase, alkaline phosphatase, acidic phosphatase, hexokinase, adenosine triphosphatase etc.

These may be used in combination.

The agent of sufficient amount and temperature and time conditions sufficient for deletion are utilized such that the ATP eluted from the microorganism and other background ATP derived from non-microbial materials can be deleted completely while the subsequent step of measuring luminescence is not adversely affected.

For example, if adenosine nucleotide deaminase is to be used, it is preferably added in an amount of 0.03 to 3 U/ml and reacted at 15 to 50° C. for 1 to 60 minutes Then, the amount of ATP in the microorganism remaining in the medium is compared with the amount of ATP in the control i.e. microorganisms cultured in a medium not containing the drug and treated in the same manner as described above in order to evaluate the drug sensitivity of the microorganisms.

Measurement of the amount of ATP in the microorganism of interest can be carried out by allowing the second ATP elution agent to act on the microorganism to extract ATP from the microorganism and measuring it using the conventional method of measuring ATP.

The second ATP elution agent is an elution agent for eluting of ATP from the microorganism of interest whose form is normal, and examples are conventionally known ATP elution agents such as surface active agents, particularly quaternary ammonium salts such as benzotrinium chloride, benzalconium chloride etc.

The method of measuring ATP includes (1) a method of determining ATP by allowing an ATP measurement reagent (referred to hereinafter as luciferin-luciferase system luminescent reagent) consisting of $Mg^{2+}$, luciferin (luminescent element) and luciferase (luminescent enzyme) to act on a sample and then determining the released bioluminescence quantitatively (see Method of Enzymatic Analysis, vol. 7, page 357, 1985), (2) a method of measuring ATP by allowing hexokinase to act on ATP in a sample in the presence of glucose to form glucose-6-posphate, then allowing glucose-6-phosphate dehydrogenase to act on the glucose-6-phosphate in the presence of NADP, and measuring the absorbance at 340 nm of the formed NADPH (see Method of Enzymatic Analysis, vol. 7, page 346, 1985), (3) a method of measuring ATP by amplifying the reaction for forming glucose-6-phosphate from D-glucose by use of a combination of hexokinase with pyruvate kinase and then quantifying ATP in terms of luminescence using 1-methoxy-5-phenazinemethyl sulfate and isoluminol (see Japanese Patent Appln. LOP Publication No. 23900/89, and (4) a method of measuring ATP by decomposing ATP into ADP and phosphoric acid with ATPase typically adenosine triphosphatase, then reacting the resulting phosphoric acid with molybdic acid to form phosphomolybdic acid, reacting the phosphomolybdic acid with ascorbic acid, and measuring the degree of blue color derived from molybdenum blue formed by reduction (see Japanese Patent Appln. LOP Publication No. 360700/92).

Among these methods, the method of determining ATP by allowing the luciferin-luciferase system luminescent reagent to act on ATP and determining the released bioluminescence quantitatively is preferable because measurement can be effected simply and rapidly to give accurate and reliable measurement results.

To carry out the above luminescent reaction smoothly, albumin, cyclodextrin, buffer agent, chelating agent etc. may be added.

As a luciferin-luciferase system luminescent reagent, any system in which ATP is required for luminescence can be utilized; for example, those derived from fireflies, UMIHOTARU, RACHIA, luminescent worms, UMISHII-TAKE etc. can be utilized; however among those derived from fireflies and from cloned microorganisms are preferable.

A reagent for determining ATP in terms of luminescence using the luciferin-luciferase system luminescent reagent and an apparatus for measuring the luminescence are commercially available, and such a commercial kit and apparatus can be used to determine ATP in the microorganism by use of luminescence in order to carry out the present invention.

One example of the luciferin-luciferase system luminescent reagent (ATP measurement solution) is as follows: 10 mM magnesium sulfate (Mg ion), 0.30 mM D-luciferin (luminescent element), 1.0 mM EDTA (stabilizer), 1.0 mM dithiothreitol (stabilizer), 0.51 mg/ml Luciola cruciata luciferase (luminescent enzyme), and 0.2% bovine serum albumin (BSA) (stabilizer), in 50 mM HEPES buffer, pH 7.8 (see page 846 in Bunseki Kagaku, Vol. 44, No 10, pp. 845–851 (1955)).

ATP in microorganisms morphologically transformed by the influence of the drug, as well as other background ATP, is deleted with the ATP deletion agent along with the first ATP elution agent; then ATP is eluted with the second ATP elution agent from the remaining microorganisms and their amount is determined using the luciferin-luciferase system luminescent go reagent; and the amount of ATP (luminescence) thus determined is compared with the amount of ATP (luminescence) in the control, i.e. microorganisms separately cultured in a drug-free medium and treated in the same manner as above, whereby the sensitivity of the microorganism to said drug is evaluated.

As compared with the control, the microorganism with a significant reduction in ATP is judged to be sensitive and the microorganism with a similar amount of ATP is judged to be resistant.

According to the present invention, there can be provided a method and a kit for testing microbial drug resistance and a method and a kit for measuring minimum inhibitory concentration for a microorganism, in which reliable evaluation results are obtained by preventing false evaluation based on false-resistance of microorganisms to a drug.

Further, according to the present invention, there can be provided a method of measuring minimum bactericidal concentration (MBC) of a drug as well as a method of measuring post antibiotic effect (PAE) of a drug, an effect that last in the absence of the drug after exposing a microorganism to the drug for a few hours.

EXAMPLES

Hereinafter, the present invention is described in more detail with reference to the following experimental examples and embodiments.

The following is one example of microorganisms examined, media, and drugs used in the experimental examples and embodiments.

(1) Medium: Cation Supplemented Mueller Hinton Broth (CSMHB) was prepared by adding $Ca^{2+}$ and $Mg^{2+}$ to Mueller Hinton Broth (Difco) at final concentrations of 50 mg/ml and 25 mg/ml respectively.

(2) Microorganism examined: A microbial suspension was obtained by culturing Pseudomonas aeruginosa ATCC 27853 overnight in the above medium and then suspending it in physiological saline at $5 \times 10^6$ CFU/ml.

(3) Drugs: Compounds known as antibiotics. Their abbreviations and general names are shown below:
FOM: Fosfomycin
ASPC: Aspoxicillin
PIPC: Piperacillin
CEZ: Cefazolin
GM: Gentamicin
TOB: Tobramycin
EM: Erythromycin
ST: Sulfamethoxazole trimethoprim
S/C: Sulbactam Cefoperazone
AZT: Aztreonam
I/C: Imipenem cilastatin
CAZ: Ceftazidime
CP: Chloramphenicol Example 1

Elution of ATP from microorganism Pseudomonas aeruginosa ATCC 27853 morphologically transformed (into filament forms) during culture in the presence of β-lactam antibiotic PIPC Experimental Method A microorganism Pseudomonas aeruginosa ATCC 27853 was inoculated at a final concentration of $5 \times 10^5$ CFU/ml in 5 ml liquid medium CSMEB containing antibiotic PIPC in an amount of 5 µg/ml (1.5 times higher concentration than minimum inhibitory concentration (MIC)), and cultured at 37° C. for 3 hours, whereby culture liquid (a) containing the microorganism morphologically transformed was obtained.

An optical micrograph of culture liquid (a) (magnification: 100X) is shown in FIG. 1.

FIG. 1 shows the form of the microorganism cultured for 3 hours in the medium containing antibiotic PIPC. Cells rendered thin and long (filament form) by the influence of the antibiotic are observed in the central vicinity.

Culture liquid (a) obtained above was divided into 5 groups (100 µl/group), and the first elution agents A to D (described below) each dissolved in 25 mM Tricine (pH 7.75) were added respectively to Groups 1 to 4, and 25 mM Tricine (pH 7.75) only as a buffer agent was added to Group 5, and they were left at room temperature for 30 minutes. (Types and concentrations of first ATP elution agents)
A: 5 mM EDTA (chelating agent)
B: 0.005% Triton X-100 (non-ionic surface active agent)
C: 0.02% ANHITOL (zwitterionic surface active agent)
D: 0.2% 2-amino-2-methyl-1,3-propanediol (amine)

Then, 50 µl luciferin-luciferase system luminescent reagent (Lucifer LU PlusTM, Kikkoman Corporation) was added and immediately measured for luminescence for a cumulated period of 3 seconds using Lumat LB9501 (Berthold Co., Ltd.).

The above luminescence is measured as the sum of the ATP eluted from the morphologically transformed microorganism with the first ATP elution agent and the background ATP originally present in the culture.

The measurement results are shown in Culture liquid (a) in Table 1 as relative values to the luminescence (as 100) in Group 5 where the microorganism was cultured in 25 mM Tricine (pH 7.75) not containing any ATP elution agent.

From the results in Table 1, the concentrations of ATP in Group 1 to 4 to which the first ATP elution was added are at least twice as high as that of Group 5 to which the first ATP elution agent was not added, so it is understood that ATP was eluted from the morphologically transformed microorganism.

Comparative Example 1

For comparison, culture liquid (b) containing the microorganism in a normal form was obtained as a control in the same manner as above except that 5 ml liquid medium CSEB not containing antibiotic PIPC was used in place of 5 ml of the above liquid medium CSMHB containing antibiotic PIPC.

Figure 2:
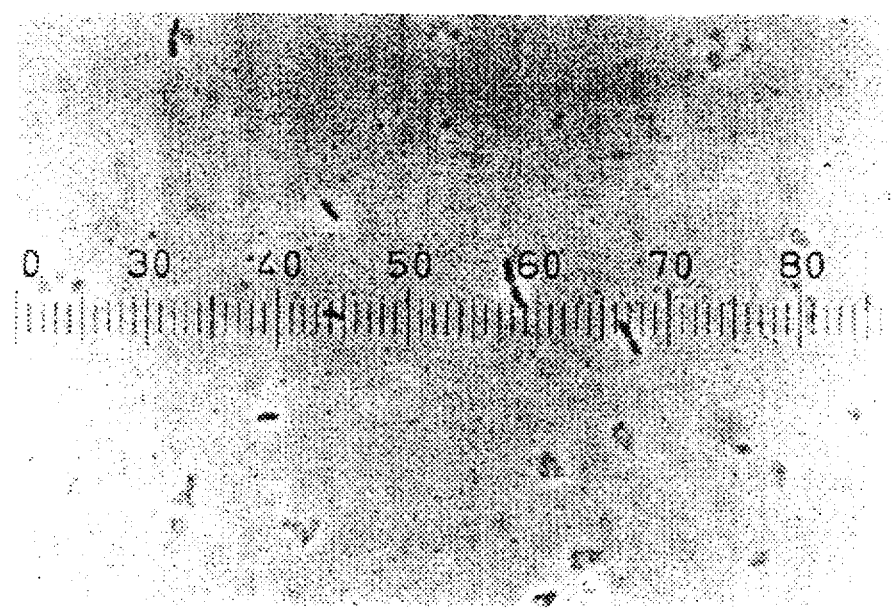
FIG. 2 is an optical micrograph (magnification: 100X) showing the form of a microorganism cultured for 3 hours in a control medium not containing antibiotic PIPC. The microorganisms in a normal form (with one elliptical cell or 2 linked cells) which are not treated with the antibiotic can be seen.

Its micrograph (magnification: 100X) is shown in FIG. 2.

FIG. 2 shows a form of the microorganism cultured for 3 hours in the control medium not containing antibiotic PIPC. The microorganisms in a normal form (with one elliptical cell or 2 linked cells) which were not treated with the antibiotic can be seen.

Then, culture liquid (b) was divided into 5 groups (100 µl/group), and the first ATP elution agents A to D dissolved in 25 mM Tricine (pH 7.75) were added respectively to Groups 1 to 4, and 25 mM Tricine (pH 7.75) only as a buffer agent was added to Group 5 and they were left at room temperature for 30 minutes.

Then, the luminescence of each control culture (b) was measured.

The results are also shown Culture (b) in Table 1.

TABLE 1

Elution or ATP from filament *P. aeruginosa* ATCC 27853 with first ATP elution agent

| First ATP Elution Agent | Culture (a) (%) | Culture (b) (%) |
|---|---|---|
| A) EDTA | 210 | 122 |
| B) Triton X-100 | 209 | 122 |
| C) Amphitol | 223 | 91 |
| D) 2-amino-2-methyl-1,3-propanediol | 457 | 117 |

Note:
The luminescence when treated with Tricine was indicated as 100%.

The results in Table 1 show that in the control culture (b), the concentrations of ATP in Groups 1 to 4 to which the first ATP elution agent was added are almost the same as that of Group 5, so it is understood that the elution of ATP from the normal microorganism did not occur even by adding the first ATP elution agent.

In contrast, culture liquid (a) of the present invention obtained by culturing in the drug-containing medium, it is understood that the concentrations of ATP in Group 1 to 4 to which the first ATP elution was added are at least twice as high as that of Group 5 to which the first ATP elution agent was not added.

From the foregoing, it is understood that any of the four first ATP elution agents described above can selectively lyse the microorganism morphologically transformed by the influence of the drug, thus eluting ATP from it.

It is further understood that the effect of 2-amino-2-methyl-1,3-propanediol is particularly outstanding.

Example 1

Preparation of a kit for testing microbial drug resistance 25 mM Tricine buffer, pH 7.75 containing 5 mM EDTA and 0.5% 2-amino-2-methyl-1,3-propanediol was prepared as a first ATP elution agent for a microorganism morphologically transformed by the influence of the drug, and 25 mM Tricine buffer, pH 7.75 containing 0.3 U/ml adenosine nucleotide deaminase was prepared as an ATP deletion agent.

Example 2

Test of drug sensitivity of *Pseudomonas aeruginosa* to β-lactam antibiotics

Drug-containing liquid medium CSMHB, to which each of the β-lactam antibiotics shown in "Type" under "Drug" in Table 2 was added at a predetermined concentration, was put to a 96-well microtiter plate (white, Dynatech CO., Ltd.) in an amount of 100 µl/well.

Then, a suspension of the microorganism *Pseudomonas aeruginosa* ATCC 27853 was inoculated aseptically into the plate in an amount of 10 µl/well (final concentration of $5 \times 10^5$ CFU/ml), and the plate was incubated at 37° C. for 3 hours.

Then, a reagent as described below containing the first ATP elution agent and the ATP deletion agent was added to the plate in an amount of 50 µl/well so that the microorganism morphologically transformed by the influence of the drug was selectively lysed thus eluting ATP from it, and simultaneously the eluted ATP and other background ATP in the medium were deleted.

(Reagent containing first ATP elution agent and ATP deletion agent)

5 mM EDTA (ATP elution agent)

0.5% 2-amino-2-methyl-1,3-propanediol (ATP elution agent)

0.3 U/ml adenosine nucleotide deaminase (ATP deletion agent)

25 mM Tricine (buffer)

pH 7.75

After the plate was left at room temperature for 30 min, 50 µl of the second ATP elution agent (0.2% benzalconium chloride) was added.

Then, 50 µl of the luciferin-luciferase system luminescent reagent (Lucifer LU Plus solved in 2.5% α-cyclodextrin) was added, and its luminescence was measured by rate assay in ML3000 (Dynatech) to measure the amount of ATP in the microorganism.

The above α-cyclodextrin was used for neutralizing the second ATP elution agent.

The amount of ATP in the microorganism as a control was determined in the same manner as above except that antibiotic-free CSMHB medium was used in place of the antibiotic-containing CSMHB medium Microbial drug sensitivity using the ATP method was evaluated by determining the ATP index. That is, the ATP index was used to evaluate microbial sensitivity and resistance using the following standards.
(Standards for Evaluation of Sensitivity S and resistance R)
ATP index=(X/Y)×100
X=luminescence from antibiotic-containing CSMHB
Y=luminescence from antibiotic-free CSMHB
ATP index≦40 : Sensitive (S)
ATP index>40 : Resistant (R)

Comparative Example 1

Tests for sensitivity of microorganism
*Pseudomonas aeruginosa* to β-lactam antibiotics by the conventional ATP method and by the conventional method For comparison, the sensitivity (susceptibility) of the microorganism *Pseudomonas aeruginosa* ATCC 27853 to β-lactam antibiotics was evaluated by the drug sensitivity test method (also referred to hereinafter as conventional ATP method) using the conventional ATP method and by the conventional method that is the micro-liquid dilution method.

The results are shown in Table 2.

The results in the conventional ATP method were obtained by adding 50 μl of the ATP extraction agent just after incubation for 3 hr and then adding 50 μl of the luciferin-luciferase system luminescent reagent to determine its luminescence and from this the ATP index was determined and evaluated.

The results of the conventional method (micro-liquid dilution method) were obtained according to the standard method regulated by the Japanese Society of Chemotherapy.

TABLE 2

Results of Sensitivity Tests of *Pseudomonas aeruginosa* ATCC 27853 to β-Lactam Antibiotics

| Drug | | Comparative Example (Conventional ATP Method) | | | Present Method | | | Conventional Method |
|---|---|---|---|---|---|---|---|---|
| Type | Concentration (μg/ml) | Luminescence (RLU) | ATP Index | Evaluation | Luminescence (RLU) | ATP Index | Evaluation | (Micro-liquid Dilution Method) |
| PIPC | 5 | 310 | 76.0 | R | 63 | 13.3 | S | S |
|  | 10 | 516 | 126.5 | R | 81 | 17.2 | S | S |
|  | 30 | 208 | 51.0 | R | 40 | 8.5 | S | S |
| S/C | 6 | 331 | 81.1 | R | 127 | 26.9 | S | S |
|  | 12.5 | 451 | 110.5 | R | 58 | 12.3 | S | S |
|  | 50 | 435 | 106.6 | R | 43 | 9.1 | S | S |
| AZT | 3 | 495 | 121.3 | R | 241 | 51.1 | R | R |
|  | 10 | 517 | 126.7 | R | 57 | 12.1 | S | S |
|  | 50 | 560 | 137.3 | R | 52 | 11.0 | S | S |
| I/C | 3 | 408 | 100.0 | R | 35 | 7.4 | S | S |
|  | 10 | 280 | 68.6 | R | 27 | 5.7 | S | S |
|  | 50 | 289 | 70.8 | R | 25 | 5.3 | S | S |
| CAZ | 3 | 578 | 141.7 | R | 54 | 11.4 | S | S |
|  | 10 | 568 | 139.2 | R | 66 | 14.0 | S | S |
|  | 100 | 566 | 138.7 | R | 21 | 4.4 | S | S |
| ASPC | 3 | 478 | 117.2 | R | 97 | 20.6 | S | S |
|  | 12.5 | 487 | 119.4 | R | 108 | 22.9 | S | S |
|  | 50 | 611 | 149.8 | R | 54 | 11.4 | S | S |
| CEZ | 3 | 226 | 55.4 | R | 358 | 75.8 | R | R |
|  | 15 | 220 | 53.9 | R | 411 | 87.1 | R | R |
|  | 60 | 241 | 59.1 | R | 391 | 82.8 | R | R |
| Control | 0 | 408 | — | — | 472 | — | — | — |

R: Resistant S: Sensitive

From the results in Table 2, the evaluation results of the test for drug sensitivity of *Pseudomonas aeruginosa* by the conventional ATP method agreed with those of the conventional method only in CEZ. For other drugs, however, the conventional ATP method indicated resistance (i.e. false-resistance) in contrast to the conventional methods, so it is understood that the evaluation results in the conventional ATP method are not reliable.

On the other hand, the method of testing microbial drug resistance using the ATP method of the present invention agreed completely with the conventional method in all drugs including CEZ.

As can be seen from the foregoing, the present invention can provide a method of testing microbial drug resistance by the ATP method, in which false evaluation in the conventional ATP method based on the false-resistance of microorganisms to a drug is prevented, so highly reliable evaluation results can be obtained.

Example 3

Test of drug sensitivity of *Pseudomonas aeruginosa* to antibiotics other than β-lactam antibiotics A test of drug sensitivity of *Pseudomonas aeruginosa* to antibiotics other than β-lactam antibiotics was carried in the same manner as in Example 2 except that the antibiotics shown in Table 3 were used in place of the β-lactam antibiotics.

Comparative Examples (The Conventional ATP Method and the Conventional Method)

For comparison, tests of resistance of *Pseudomonas aeruginosa* to antibiotics other than β-lactam antibiotics were carried out using the conventional ATP method and the conventional method (i.e. the micro-liquid dilution method) in the same manner as in Comparative Example 1.

The results are shown in Table 3.

The evaluation results of the present method, the conventional ATP method and the conventional method are collectively shown in Table 3.

TABLE 3

Results of Sensitivity Tests of *Pseudomonas aeruginosa* ATCC 27853 to Antibiotics Other Than β-Lactam Antibiotics

| Drug | | Comparative Example | Present Method | Conventional Method |
|---|---|---|---|---|
| Type | Concentration (μg/ml) | (Conventional ATP Method) | | (Micro-liquid Dilution Method) |
| FOM | 10 | R | S | S |
| | 50 | R | S | S |
| | 200 | R | S | S |
| GM | 5 | S | S | S |
| | 10 | S | S | S |
| | 30 | S | S | S |
| TOB | 2 | S | S | S |
| | 10 | S | S | S |
| | 50 | S | S | S |
| EM | 2 | R | R | R |
| | 5 | R | R | R |
| | 30 | R | R | R |
| CP | 1 | R | R | R |
| | 5 | R | R | R |
| | 60 | R | R | R |
| ST | 10 | R | R | R |
| | 50 | S | R | R |
| | 200 | S | S | S |

R: Resistant S: Sensitive

As can be seen from the results in Table 3, the evaluation results of the conventional method are sensitive to antibiotic FOM (phosphomycin) other than β-lactam antibiotics, at all concentrations while the corresponding evaluation result of the conventional ATP method is resistant. Further, the evaluation result of the conventional method is resistant to antibiotic ST (sulfamethoxazol trimethoprim) at a concentration of 50 μg/ml, while the corresponding evaluation result of the conventional ATP method is sensitive. Hence, it is understood that the reliability of the evaluation results is undermined. On the other hand, the method of testing microbial drug sensitivity using the ATP method of the present invention agreed in all groups with the conventional method.

The ATP method of the present invention also agreed with the conventional method even in other drugs for which the conventional ATP method agreed with the conventional method.

The present invention can provide a method of testing microbial drug resistance of *Pseudomonas aeruginosa* even for antibiotics other than β-lactam antibiotics, in which false evaluation based on the false-resistance of the microorganism to a drug is prevented, so highly reliable evaluation results can be obtained. As can be seen from the above results, the method of testing microbial drug resistance according to the present invention can be applied not only to β-lactam antibiotics but also to a wide spectrum of drugs.

Example 4

Test of drug sensitivity of microorganisms other than *Pseudomonas aeruginosa*

Microorganisms other than *Pseudomonas aeruginosa*, that is, *Escherichia coli* ATCC 25922, *Staphylococcus aureus* ATCC 25923 and *Enterococcus faecalis* ATCC 29212 were used as microorganisms examined, and their sensitivity to the respective drugs shown in Table 4 were evaluated by the method of testing drug sensitivity using the conventional ATP method and by the method of testing drug sensitivity using the ATP method of the present invention. A correlation of these methods with the micro-liquid dilution method as the conventional method (standard method) was examined by comparing their results.

Measurements were carried out in the same manner as in Example 2.

The evaluation results in the respective measurement methods are shown in Table 4.

TABLE 4

Results of Sensitivity Tests of Microorganisms Other Than *Pseudomonas aeruginosa* to Antibiotics

| Micro-organism | Drug | | Comparative Example (Conventional ATP Method) | Present Method | Conventional Method (Micro-liquid Dilution Method) |
|---|---|---|---|---|---|
| | Type | Concentration (μg/ml) | | | |
| *E. coli* ATCC 25922 | PIPC | 5 | R | S | S |
| | | 10 | R | S | S |
| | | 30 | R | S | S |
| | AZT | 3 | R | S | S |
| | | 10 | R | S | S |
| | | 50 | S | S | S |
| | CAZ | 3 | R | S | S |
| | | 10 | S | S | S |
| | | 100 | S | S | S |
| | EM | 2 | R | R | R |
| | | 5 | R | R | R |
| | | 30 | S | S | S |
| *S. aureus* ATCC 25923 | PIPC | 5 | S | S | S |
| | | 10 | S | S | S |
| | | 30 | S | S | S |
| | AZT | 3 | R | R | R |
| | | 10 | R | R | R |
| | | 50 | R | R | R |
| | CAZ | 3 | R | R | R |
| | | 10 | S | S | S |
| | | 100 | S | S | S |
| | EM | 2 | S | S | S |
| | | 5 | S | S | S |
| | | 30 | S | S | S |
| *E. faecalis* ATCC 29212 | PIPC | 5 | S | S | S |
| | | 10 | S | S | S |
| | | 30 | S | S | S |
| | AZT | 3 | R | R | R |
| | | 10 | R | R | R |
| | | 50 | R | R | R |
| | CAZ | 3 | R | R | R |
| | | 10 | R | R | R |
| | | 100 | S | S | S |
| | EM | 2 | S | S | S |
| | | 5 | S | S | S |
| | | 30 | S | S | S |

R: Resistant S: Sensitive

As can be seen from the results in Table 4, the conventional ATP method indicated false-resistance to β-lactam antibiotics (drugs) PIPC, AZT and CAZ where the microorganism examined was *Escherichia coli* ATCC 25922.

However, the method of the present invention was free of such false-resistance, and a complete correlation of the present method with the conventional method was obtained. The ATP method of the present invention also agreed with the conventional method even in the other microorganisms for which the conventional ATP method agreed with the conventional method.

That is, it is understood that the present invention can provide a method of testing microbial drug resistance with high reliability for a wide spectrum of microorganisms not limited to *Pseudomonas aeruginosa* and for a wide variety of drugs.

Example 5

Kit for measuring minimum inhibitory concentration for microorganisms

The following compounds (A) and (B) were used in 25 mM Tricine buffer, pH 7.55.

(A) First ATP elution agent for microorganism morphologically transformed by the influence of drugs:
5 mM EDTA; and
0.5% 2-amino-2-methyl-1,3-propanediol.

(B) ATP deletion agent:
0.3 U/ml adenosine phosphate deaminase.

Example 6

Measurement of minimum inhibitory concentration (MIC) for a microorganism

Minimum inhibitory concentration for each of the drugs shown in Table 5 for the microorganism Pseudomonas aeruginosa ATCC 27853 was determined by the method of the present invention, and its correlation with the micro-liquid dilution method and the agar plate dilution methods as the conventional methods (standard methods) was examined.

Two-fold serial dilutions of 100 µg/ml to 0.1 µg/ml of drugs shown in Table 5 were prepared in CSMHB and put to a 96-well microtiter plate (whites Dynatech Co., Ltd.) in an amount of 100 µl/well.

The sensitivity of the microorganism Pseudomonas aeruginosa ATCC 27853 to each drug at each concentration was evaluated by the method as indicated in Example 2.

The lowest drug concentration at which the microorganism was evaluated to be sensitive was determined as the minimum inhibitory concentration for the microorganism.

The conventional method was evaluated according to the standard method regulated by the Japanese Society of Chemotherapy.

The results are shown in Table 5.

TABLE 5

Measurement Results of Maximum Inhibitory Concentration for Microorganism Pseudomonas aeruginosa ATCC 27853

| | Maximum Inhibitory Concentration (µg/ml) | | |
| --- | --- | --- | --- |
| Drug | Present Method | Conventional Method 1 (Micro-liquid Dilution Method) | Conventional Method 2 (Agar Plate Dilution Method) |
| ASPC | 25 | 100 | 50 |
| PIPC | 1.56 | 3.13 | 3.13 |
| I/C | 0.78 | 1.56 | 1.56 |
| CEZ | >100 | >100 | >100 |
| MINO | 6.25 | 50 | 12.5 |
| EM | 100 | >100 | >100 |
| CP | 50 | >100 | 100 |
| ST | >100 | >100 | >100 |

As can be seen from the results in Table 5, the measurement values of minimum inhibitory concentration for the microorganism according to the present invention agreed with those of the conventional methods (micro-liquid dilution method and agar plate dilution method), with a measurement error within plus or minus 2 stages.

From the foregoing, it is understood that the method of measuring minimum inhibitory concentration for microorganisms with highly reliable evaluation results can be provided according to the present invention.

In summary, according to the present invention, a method and a kit for testing microbial drug resistance and a method and a kit for measuring minimum inhibitory concentration for a microorganism, in which highly reliable evaluation results are obtained by preventing false evaluation based on false-resistance of the microorganism to a drug, are presented.

Further, according to the present invention, a highly reliable method of measuring the post-antibiotic effect (PAE) an effect that continues even after a microorganism is subjected to a drug for a short period of time and then freed from this drug and a highly reliable method of measuring the minimum bactericidal concentration (MBC) of a drug are presented.

What is claimed is:

1. A method of testing sensitivity to an antimicrobial agent, comprising:

(a) inoculating and culturing a microorganism in a medium containing an antimicrobial agent;

(b) adding a first ATP elution agent, wherein said first ATP elution agent is capable of eluting ATP from a morphologically transformed, but not a morphologically untransformed microorganism and an ATP deletion agent to obtain a resulting culture;

(c) adding a second ATP elution agent to the resulting culture obtained in step (b) and determining the eluted ATP, wherein said second ATP elution agent is capable of eluting ATP from morphologically untransformed forms of said microorganism;

(d) inoculating and culturing a microorganism in a control medium not containing said anti-microbial agent, and carrying out steps (b) and (c) to determine the ATP in the microorganism; and (e) comparing the amounts of ATP obtained in steps (c) and (d), wherein the difference in eluted ATP determined in steps (c) and (d) above correlates to the sensitivity of said microorganism to said antimicrobial agent.

2. The method of claim 1, wherein the first ATP elution agent is selected from the group consisting of a chelating agent, a surface active agent, and an amine.

3. The method of claim 2 wherein the amine is selected from the group consisting of 2-amino-2-methyl-1,3-propanediol, 2-amino-2-methyl-1-propanol, ethylamine, and ethanolamine.

4. The method of claim 1, wherein said microorganism is gram negative.

5. The method of claim 1, wherein said microorganism is selected from the group consisting of Pseudomonas aeuroginosa, Escherichia coli, Staphylococcus aureus, and Enterococcus faecalis.

6. The method of claim 1, wherein determining the amount of ATP is performed using an assay selected from the group consisting of a luciferin-luciferase system luminescent reagent, a hexokinase reaction, a hexokinase/pyruvate kinase reaction, and an adenosine triphosphatase reaction.

7. A method of measuring a minimum inhibitory concentration of an anti-microbial agent for a microorganism, comprising:

(a) providing a plurality of media comprising said antimicrobial agent at a plurality of concentrations;

(b) inoculating and culturing a microorganism in each medium containing said antimicrobial agent;

(c) adding a first ATP elution agent wherein said first ATP elution agent is capable of eluting ATP from a morphologically transformed form but not a morphologically untransformed form, of a microorganism, and an ATP deletion agent to the resulting culture;

(d) adding a second ATP elution agent to the culture obtained in step (c) above and determining the eluted ATP, wherein said second ATP elution agent is capable of eluting ATP from morphologically untransformmed forms of said microorganism;

(e) inoculating and culturing a microorganism in a control medium not containing said antimicrobial agent, and carrying out steps (c) and (d) to determine the ATP in the microorganism; and (f) comparing the amounts of ATP obtained in steps (d) and (e), wherein the least detectable difference between the eluted ATP determined in steps (d) and (e) above correlates with the minimum inhibitory concentration of said antimicrobial agent.

8. The method of claim 7 wherein the first ATP elution agent is selected from the group consisting of a chelating agent, a surface active agent, and an amine.

9. The method of claim 7, wherein said microorganism is gram negative.

10. The method of claim 7, wherein said microorganism is selected from the group consisting of *Pseudomonas aeuroginosa, Escherichia coli, Staphylococcus aureus,* and *Enterococcus faecalis.*

11. The method of claim 7, wherein determining the amount of ATP is performed using an assay selected from the group consisting of a luciferin-luciferase system luminescent reagent, a hexokinase reaction, a hexokinase/pyruvate kinase reaction, and an adenosine triphosphatase reaction.

12. A kit for testing sensitivity to an antimicrobial agent, comprising a carrier means containing one or more containers comprising a first container containing a first ATP elution agent, wherein said first ATP elution agent is capable of eluting ATP from a morphologically transformed, but not an morphologically untransformed form of a microorganism; and a second container containing an ATP deletion agent.

13. The kit of claim 12, further comprising:

a third container containing a second ATP elution agent, wherein said second ATP elution agent is capable of eluting ATP from morphologically untransformed forms of said microorganism; and a fourth container containing a luciferin-luciferase system luminescent reagent.

* * * * *